US010555796B2

(12) United States Patent
Chodorow

(10) Patent No.: US 10,555,796 B2
(45) Date of Patent: Feb. 11, 2020

(54) FLOSSER DISPENSER

(71) Applicant: Sacks Holdings, Inc., Solana Beach, CA (US)

(72) Inventor: Devin S. Chodorow, San Diego, CA (US)

(73) Assignee: Sacks Holdings, Inc., San Diego, CA (US)

( * ) Notice: Subject to any disclaimer, the term of this patent is extended or adjusted under 35 U.S.C. 154(b) by 92 days.

(21) Appl. No.: 15/098,166

(22) Filed: Apr. 13, 2016

(65) Prior Publication Data

US 2016/0361147 A1    Dec. 15, 2016

Related U.S. Application Data

(60) Provisional application No. 62/146,557, filed on Apr. 13, 2015.

(51) Int. Cl.
*A61C 15/04* (2006.01)

(52) U.S. Cl.
CPC .......... *A61C 15/043* (2013.01); *A61C 15/046* (2013.01)

(58) Field of Classification Search
CPC .......... A45D 44/18; A47K 1/09; A61C 15/04; A61C 15/043; A61Q 11/00
See application file for complete search history.

(56) References Cited

U.S. PATENT DOCUMENTS

| | | | | |
|---|---|---|---|---|
| 2,215,850 A | * | 9/1940 | Holdeman | A47F 1/10 211/59.2 |
| 3,251,188 A | * | 5/1966 | Dean | A47F 3/0486 221/92 |
| 5,732,820 A | * | 3/1998 | Tsai | B65D 43/20 206/369 |
| 5,738,124 A | * | 4/1998 | Cervato | A61C 15/043 132/323 |
| 6,152,147 A | * | 11/2000 | Sanchez | A61C 15/00 132/323 |
| D437,977 S | * | 2/2001 | Lang | D28/66 |
| 2001/0054563 A1 | * | 12/2001 | Lang | A61C 15/00 206/369 |
| 2005/0236011 A1 | * | 10/2005 | Chodorow | A61C 15/046 132/327 |
| 2008/0295859 A1 | * | 12/2008 | Grendol | A61C 15/043 132/324 |
| 2012/0325690 A1 | * | 12/2012 | Brodkin | B65D 73/0028 206/63.5 |

(Continued)

*Primary Examiner* — Gene O Crawford
*Assistant Examiner* — Kelvin L Randall, Jr.
(74) *Attorney, Agent, or Firm* — Kilpatrick, Townsend and Stockton LLP

(57) ABSTRACT

Dental tool storage systems and containers are disclosed herein. A dental tool storage system can include a plurality of flossers that can include a flossing head having: a first arm; a second arm; a connecting member; and a filament extending from the first arm to the second arm; and a handle portion extending from the flossing head. The dental tool storage system can include a dental tool storage container having an internal volume defined by: a top; a bottom; and a plurality of sides. The internal volume can be sized and shaped to receive the plurality of flossers in a stack extending at least partially between the top and bottom of the internal volume. The dental tool storage unit can include a dispensing feature and a fixation feature.

11 Claims, 10 Drawing Sheets

(56) References Cited

U.S. PATENT DOCUMENTS

2014/0000647 A1\* 1/2014 Stewart ................ A61C 15/046
132/324
2017/0100222 A1\* 4/2017 Kalbfeld .............. A61C 15/046

\* cited by examiner

FLOSSER DISPENSER

CROSS-REFERENCES TO RELATED APPLICATIONS

This application claims the benefit of U.S. Provisional Application No. 62/146,557 entitled "FLOSSER DISPENSER," and filed on Apr. 13, 2015, the entirety of which is hereby incorporated by reference herein.

BACKGROUND OF THE INVENTION

The present invention relates, generally, to dental devices, and more particularly to dental hygiene devices.

While dental hygiene has long been important in American and other cultures for maintaining a desirable physical appearance, recent discoveries have increased the urgency with which dental hygiene is maintained. These recent discoveries have linked oral bacteria to other, more serious diseases such as, for example, heart disease. In light of the increased importance of dental hygiene, new devices are desired to improve dental hygiene.

BRIEF SUMMARY OF THE INVENTION

One aspect of the present disclosure relates to a dental tool storage system. The dental tool storage system includes: a plurality of flossers. The flossers have: a flossing head having: a first arm; a second arm; a connecting member; and a filament extending from the first arm to the second arm; and a handle portion extending from the flossing head. The dental tool storage system includes a dental tool storage container. The dental tool storage container includes: an internal volume defined by: a top; a bottom; and a plurality of sides. In some embodiments, the internal volume is sized and shaped to receive the plurality of flossers in a stack extending at least partially between the top and bottom of the internal volume. The dental tool storage container includes: a dispensing feature located in one of: the top; the bottom; or one or more of the plurality of sides, which dispensing feature is sized and shaped to simultaneously dispense a desired number of flossers; and a fixation feature extending at least partially from one of: the top; or bottom, towards the other of the top or bottom, which fixation feature is sized and shaped to engage with at least some of the plurality of flossers to fix the position of the at least some of the plurality of flossers with respect to the plurality of sides.

In some embodiments, wherein the fixation features include a fixation post. In some embodiments, the fixation post is sized to fit between the first arm, the second arm, and the filament of the flossing head. In some embodiments, the fixation post connects to the bottom of the dental tool storage system and is separated from the top of the dental tool storage container by a space. In some embodiments, the space is greater than the thickness of one flosser and less than the thickness of two flossers.

In some embodiments, the fixation features include a plurality of fixation posts. In some embodiments, the plurality of fixation posts are positioned to engage the exterior of the flossing head of the flosser. In some embodiments, the fixation features hold a first flosser in a first orientation and a second flosser in a second orientation. In some embodiments, the flossing head of the first flosser is proximate to the handle of the second flosser when the first flosser is in the first orientation and when the second flosser is in the second orientation.

In some embodiments, the dispensing features include at least one of: a dispensing aperture; a door; a corner kickout; and a manual actuator. In some embodiments, the dispensing features include at least one of: a threaded positioning element; a spring-loaded platform; a spring-ratchet mechanism; and a ratchet mechanism.

One aspect of the present disclosure relates to a dental tool storage container. The dental tool storage container includes: an internal volume defined by: a top; a bottom; and a plurality of sides. In some embodiments, the internal volume is sized and shaped to receive a plurality of dental tools in a stack extending at least partially between the top and bottom of the internal volume. The dental tool storage container includes: a dispensing feature located in one of: the top; the bottom; or one or more of the plurality of sides, which dispensing feature is sized and shaped to simultaneously dispense a desired number of dental tools; and a fixation feature extending at least partially from one of: the top; or bottom towards the other of the top or bottom. In some embodiments, the fixation features are sized and shaped to engage with at least some of the plurality of dental tools to fix the position of the at least some of the plurality of dental tools with respect to the plurality of sides.

In some embodiments, the fixation feature includes a fixation post. In some embodiments, the fixation post is sized to fit in an interior portion of the dental tool. In some embodiments, the fixation post connects to the bottom of the dental tool storage container and is separated from the top of the dental tool storage container by a space. In some embodiments, the space is greater than the thickness of one dental tool and less than the thickness of two dental tools.

In some embodiments, the fixation feature includes a plurality of fixation posts. In some embodiments, the plurality of fixation posts are positioned to engage an exterior of the dental tools. In some embodiments, the fixation feature holds first dental tools in a first orientation and second dental tools in a second orientation. In some embodiments, the dispensing features include: first dispensing features for dispensing first dental tools; and second dispensing features for dispensing second tools.

In some embodiments, the dispensing features include at least one of: a dispensing aperture; one or more doors; a corner kickout; and a manual actuator. In some embodiments, the dispensing features include at least one of: a threaded positioning element; a spring-loaded platform; a spring-ratchet mechanism; and a ratchet mechanism.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION OF THE INVENTION

In some embodiments, the present disclosure relates to a dental tool storage container. The dental tool storage container can be sized and shaped, and include features to facilitate the orderly storage of a plurality of dental tools such as, for example, dental flossers, floss picks, interdental tools, interproximal tools, or the like. In some embodiments, the dental tool storage container can include features configured to fix the position and/or the orientation of one or several dental tools, to control the delivery of dental tools such that, for example, only 1, 2, 3, 4, 5, 10, and/or any other or intermediate number of dental tools is delivered at a time.

In some embodiments, the features configured to fix the orientation of the one or several dental tools can comprise, for example, one or several fixation posts and/or one or several fixation walls or tabs. In some embodiments, all of portions of the features configured to fix the orientation of one or several dental tools can engage a flossing head of the dental tool and/or a handle portion of the flossing tool. In some embodiments, all of portions of the features configured to fix the orientation of one or several dental tools can simultaneously engage the flossing head and the handle portion of the flossing tool.

In some embodiments, a fixation post can be sized and shaped to be received within a flossing head of the dental tool. In some embodiments, the fixation post can engage with portions of the flossing head of the dental tool such that the orientation of the dental with respect to the dental tool storage container is fixed.

In some embodiments, one or several features of the dental tool storage container can be configured to control the delivery of the dental tool from the dental tool storage container. In some embodiments, this can include preventing a user of the dental tool storage container from touching more of the dental tools than are delivered and/or can include limiting the number of dental tools delivered at one time. In some embodiments, these one or several features can include a door or opening sized to only allow the delivery of the desired number of dental tools, a push button or push tab sized to deliver the desired number of dental tools, and/or the like.

Figure 1:
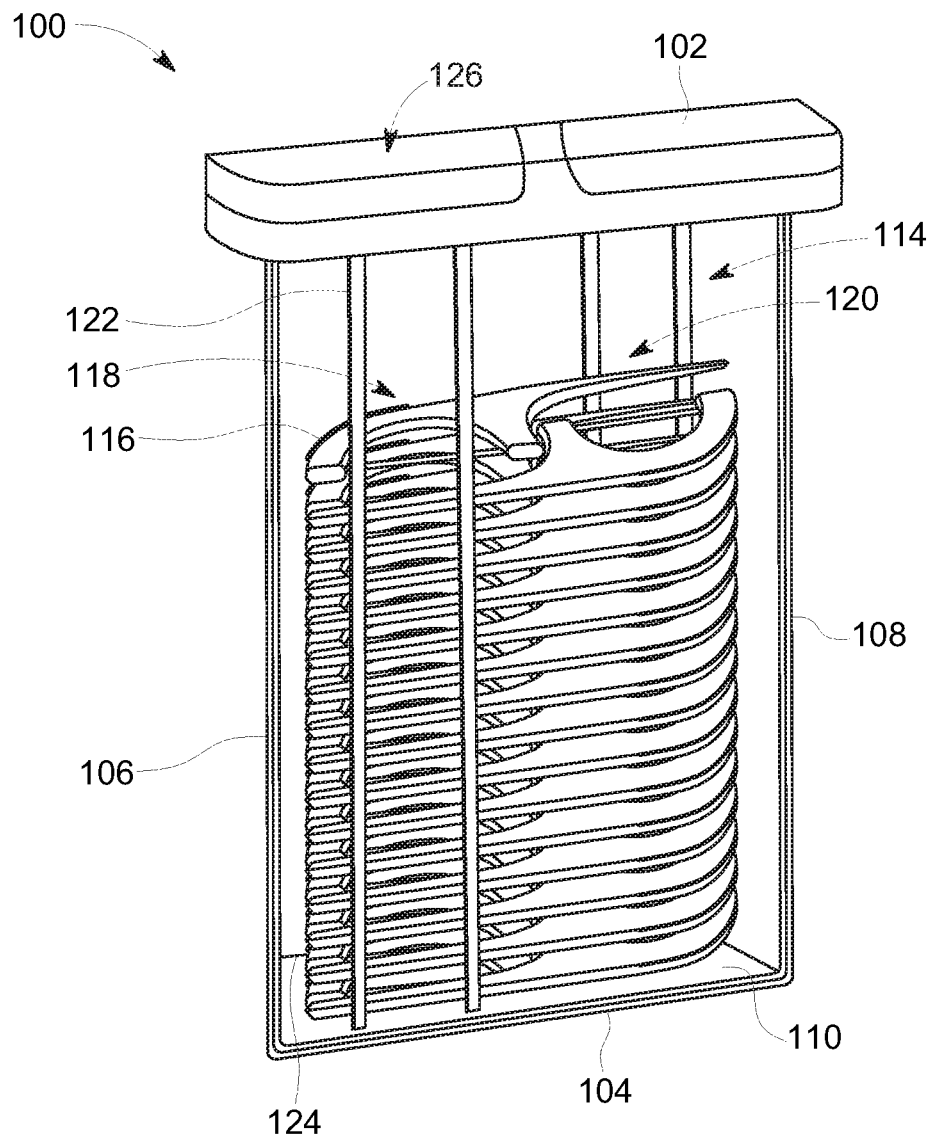
FIG. 1 is a perspective view of one embodiment of a dental tool storage container.

With reference now to FIG. 1, a perspective view of one embodiment of a dental tool storage container 100 is shown. The dental tool storage container 100 can comprise a variety of shapes and sizes and can be made from a variety of materials such as, for example, a metal or metal alloy, paper, cardboard, wood, a polymer including, for example, a transparent or non-transparent plastic, or the like. In some embodiments, all or portions of the dental tool storage container 100 can be made from a single piece, and in some embodiments, all or portions of the dental tool storage container 100 can be made from multiple pieces. In one embodiment, for example, the dental tool storage container 100 can comprise a clamshell container.

The dental tool storage container 100 includes a top 102, a bottom 104, and a plurality of sides including, for example: a first side 106; a second side 108; a front 110; and a back (not shown). Together, the top 102, the bottom 104, the first side 106, the second side 108, the front 110, and the back define an internal volume 114. In some embodiments, the internal volume 114 of the dental tool storage container 100 can be sized and shaped, via the sizing and shaping of one or several of: the top 102; the bottom 104; and the plurality of sides, to receive a plurality of dental tools such as, for example, flossers 116. In some embodiments, the internal volume 114 of the dental tool storage container 100 can be sized and shaped to receive a plurality of dental tools in a stack extending at least partially from the top 102 to the bottom 104 of the dental tool storage container 100. In some embodiments, the dental tools in the stack can be separated by one or several dividers, which dividers can be paper, fabric, cardboard, polymer, or any other desired material. In some embodiments in which the dental tool storage container 100 comprises a clamshell container, the front 110 can be on one side of the clamshell, and the back can be on the other side of the clamshell. In some such embodiments, the clamshell can mate on one or more of: the top 102, the bottom 104, the first side 106, and the second side 108. In some embodiments, the dental tool storage container 100 can comprise a removable tray. In some embodiments, the removable tray can be loaded with, for example, one or several dental tools, and the tray and the dental tools can then be loaded into the internal volume 114 of the dental tool storage container 100.

Figure 1A:
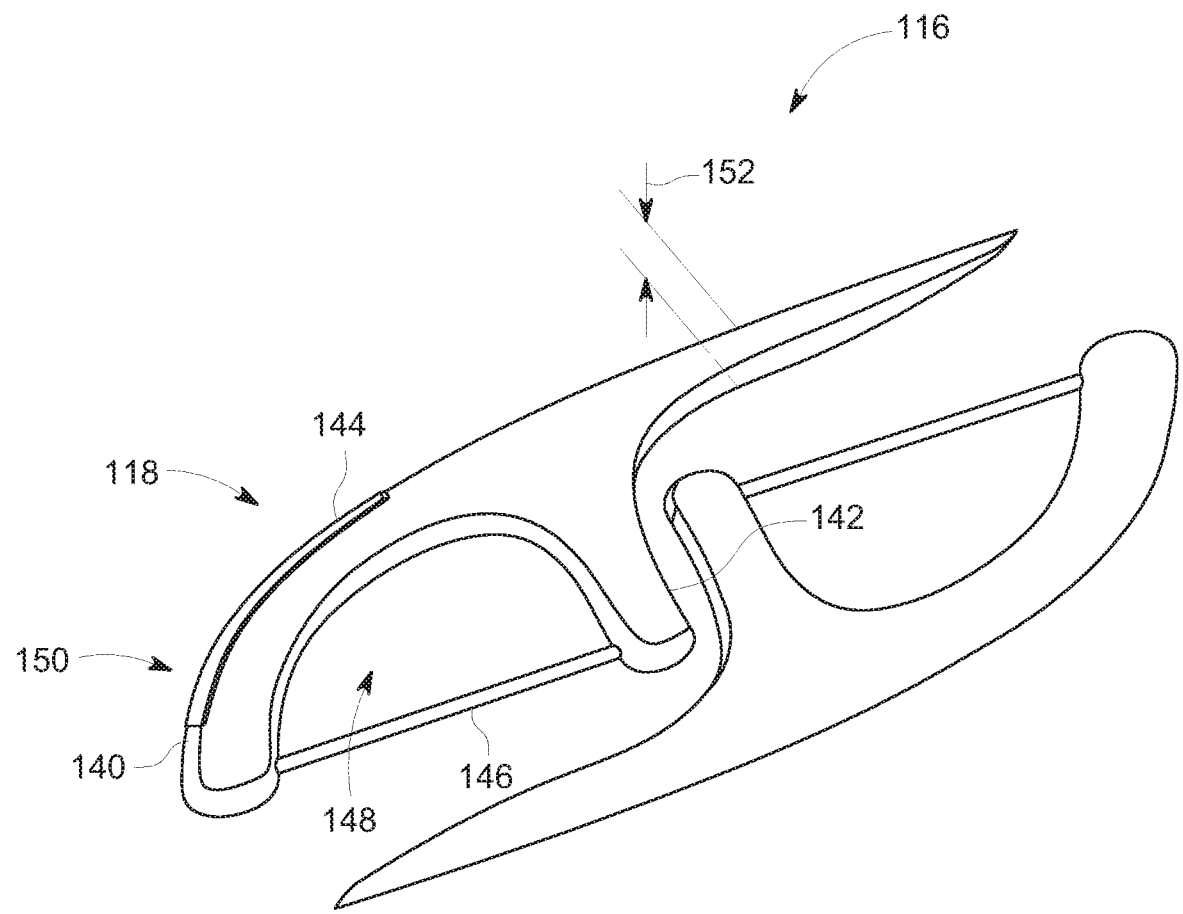
FIG. 1A is a perspective view of one embodiment of a flosser.

With reference now to FIG. 1A, the flossers 116 can comprise a variety of shapes and sizes. In some embodiments, the flossers 116 can comprise a flossing head 118 that can include, for example, a first arm 140, a second arm 142, a connecting arm 144 linking the first arm 140 and the second arm 142, and a filament 146 extending between the first and second arms 140, 142. The flosser 116 can include an interior portion 148 defined by the interior surfaces of the first and second arms 140, 142, the connecting arm 144, and the filament 146, and an exterior portion 150. The flosser 116 can further include a handle portion 120. In some embodiments, the handle portion 120 can comprise a first end attaching to the flossing head 118 and a second end distal from the flossing head 118. In some embodiments, the second end of the handle portion 120 can comprise a point such as, for example, a pick. The flosser 116 can further comprise a thickness 152.

The flossers 116 can be made from a variety of materials. In some embodiments, the flossers 116 can comprise a polymer, and the filament can comprise a lubricious fiber. In some embodiments, the flosser 116 can be created via any desired manufacturing process such as, for example, injection molding.

In some embodiments, the dental tool storage container 100 can include one or several fixation features that can fix the orientation of the flossers 116 contained in the internal volume 114 with respect to one or several features of the dental tool storage container 100 such as, for example, the first side 106, the second side 108, the front 110, and/or the back. In some embodiments, these one or several fixation features can extend through all of part of the internal volume 114 and can engage with all potions of the flossers 116. In some embodiments, for example, these one or several fixation features can engage with all of portions of the flossing head 118 and/or all or portions of the handle 120. In some embodiments in which the dental tool storage container 100 comprises a tray, some or all of the fixation features can be located on the tray.

In some embodiments, the fixations portions can comprise a fixation post 122, and in some embodiments, the fixation portions can comprise a plurality of fixation posts 122. A fixation post 122 can comprise a member, which can be a part of the dental tool storage container 100 that can engage with a portion of the dental tool to secure the position or orientation of the dental toll with respect to one or several portions of the dental tool storage container 100. The fixation post 122 can, in some embodiments, extend from the bottom 104 of the dental tool storage container 100 towards the top 102 of the dental tool storage container 100. In some embodiments, the fixation post 122 can be connected to the bottom 104 of the dental tool storage container 100 and disconnected from the top 102 of the dental tool storage container 100.

The fixation post 122 can comprise the same materials as other portions of the dental tool storage container 100 such as, for example, as the bottom 104, first side 106, the second side 108, the front 110, and/or the back, and in some embodiments, the fixation post 122 can comprise a different material.

The fixation post 122 can comprise a variety of shapes and sizes. In some embodiments, the fixation post 122 can be sized and shaped to engage with a portion of the flossing head 118. In some embodiments, the fixations post(s) 122 can be sized, shaped, and/or positioned to: engage with the external surfaces of the flossing head (i.e. surfaces other than those surfaces that define or bound the portion of the flossing head 118 between the first and second arms and the filament), engage with internal surfaces of the flossing head 118 or flosser 116, and/or to engage with all or portions of the handle 120.

In some embodiments, the fixation post can be sized and shaped to be received within the flossing head between the first and second arms and the filament extending between the first and second arms. In some embodiments, the fixation post 122 can be sized to snugly fit within the flossing head 118 such that the flossers 116 are held in place along the fixation post 122 unless a force arising from an acceleration of the dental tool storage container 100 or from contact with one or several of the flossers 116 is applied to the flossers 116, and in some embodiments, the fixation post 122 can be sized to fit loosely within the flossing head 118 such that gravity can displace the flossers 116 along the fixation post 122 so as to allow gravity feeding of the flossers 116 along the fixation post 122.

The fixation portions can, in some embodiments, include a handle fixation feature 124. The handle fixation feature 124 can, in some embodiments, extend from the bottom 104 of the dental tool storage container 100 towards the top 102 of the dental tool storage container 100. In some embodiments, the handle fixation feature 124 can be connected to the bottom 104 of the dental tool storage container 100 and disconnected from the top 102 of the dental tool storage container 100, and in some embodiments, the handle fixation feature 124 can be connected to one or both of the top 102 and the bottom 104 of the dental tool storage container 100.

The handle fixation feature 124 can comprise the same materials as other portions of the dental tool storage container 100 such as, for example, as the bottom 104, first side 106, the second side 108, the front 110, and/or the back, and in some embodiments, the handle fixation feature 124 can comprise a different material. In some embodiments, the handle fixation feature 124 can comprise one or several a planar surfaces that engage with all or portions of the handle 120 of the flosser 116. In some embodiments, the handle fixation feature 124 can be sized, shaped, and/or positioned to prevent the rotation of the flossers 116 about the fixation post 122. In some embodiments, the planar surface of the handle fixation feature 124 can be positioned with respect to one of the front 110 and the back of the dental tool storage container 100 such that the handles 120 of the flossers 116 are held between the planar surface and the one of the front 110 and the back of the dental tool storage container 100.

In some embodiments, the fixation features of the dental tool storage container 100 can be configured to hold all of the flossers 116 in the internal volume 114 in a single orientation, and in some embodiments, the fixation features of the dental tool storage container 100 can be configured to hold the flossers 116 in multiple orientations within the internal volume 114. In one embodiment, for example, the fixation features can comprise a first fixation post proximate to the first side 106 that holds some flossers 116 in a first orientation with their flossing heads 118 proximate to the first side 106 of the dental tool storage container 100, and the fixation features can comprise a second fixation post proximate to the second side 108 that holds some flossers 117 in a second orientation with their flossing heads 118 proximate to the second side 108 of the dental tool storage container 100. In some embodiments, the handles 120 of the flossers 116 in the first orientation can be held proximate to the back of the dental tool storage container 100, and the handles 120 of the flossers in the second orientation can be held proximate to the front of the dental tool storage container 100. In such an embodiment, flossers 116 can be alternatingly stacked such that flossing head 118 of one flosser 116 is proximate to the handles 120 of adjacent flossers 116, and the handle 120 of the one flosser 116 is proximate to the flossing heads 118 of the adjacent flossers 116. In some embodiments, some embodiments, the flossers 116 can be stacked in two adjacent stacks within the dental tool storage container 100. In some embodiments, the first of the two adjacent stacks can comprise flossers 116 in the first orientation and the second of the two adjacent stacks can comprises flossers 116 in the second orientation. In some such embodiments in which different groups of flossers 116 are held in different orientations unused space within the internal volume 114 of the dental tool storage container 100 can be minimized.

The dental tool storage container 100 can include one or several dispensing features 126. In some embodiments, the dispensing features 126 can be one or several features that allow the removal of a desired number of the dental tools from the internal volume 114 of the dental tool storage container 100. In some embodiments, these dispensing features 126 can be configured to allow the removal of 1, 2, 3, 4, 5, 6, 7, 8, 9, 10, and/or any other number of dental tools simultaneously from the internal volume 114 of the dental tool storage container 100.

The dental tool storage container 100 can include one or several connection features 128. In some embodiments, the connection features can be configured to allow the connection of multiple dental tool storage containers 100. In some embodiments, a dental tool storage container 100 can include a plurality of connection features 128 to connect with a plurality of other dental tool storage container 100. In such an embodiment, for example, the connection features 128 can comprise, for example: first connection features located on the first side 106 of the dental tool storage container 100 and second connection features located on the second side of the dental tool storage container 100; first connection features located on the front 110 of the dental tool storage container 100 and second connection features located on the back of the dental tool storage container 100; and/or the like.

Figure 1B:
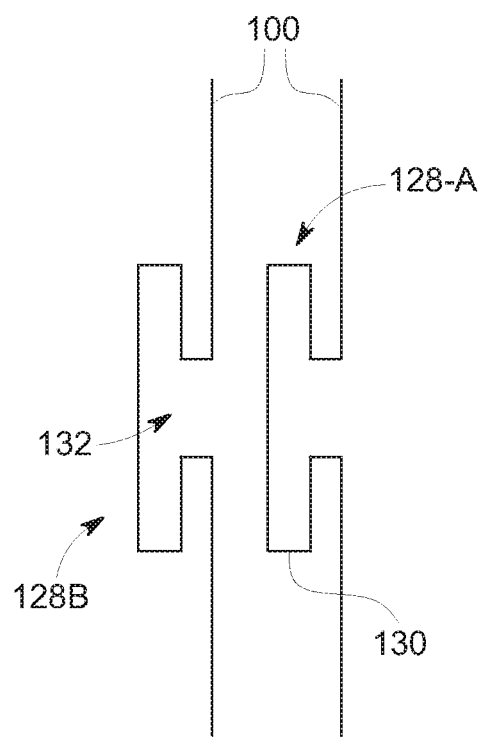
FIG. 1B is a top view of one embodiment of connection features.

The connection features 128 can comprise a variety of shapes and sizes and can include any features of one dental tool storage container 100 that can matingly engage with connection features 128 of another dental tool storage container 100 to reattachably connect the dental tool storage containers 100. These features can include, for example, one or several snaps, clips, friction-fit features, force-fit features, or the like. One embodiment of the connection features 128 is shown in FIG. 1B. As seen in FIG. 1B, the connection features 128 can include a male connector 128-A and a female connector 128-B. The male connector 128-A can include a tab 130 that can be received in a channel 132 of the female connector 128-B.

With reference now to FIGS. 2-8, different embodiments of dispensing features are shown. In some embodiments, one or several of the dispensing features shown in FIGS. 2-8 can be combined one or several others of the dispensing features shown in those same figures. In some embodiments, these combinations can be the same as shown in FIGS. 2-8, and in some embodiments, these combinations can be different than those embodiments shown in FIGS. 2-8.

Figure 2:
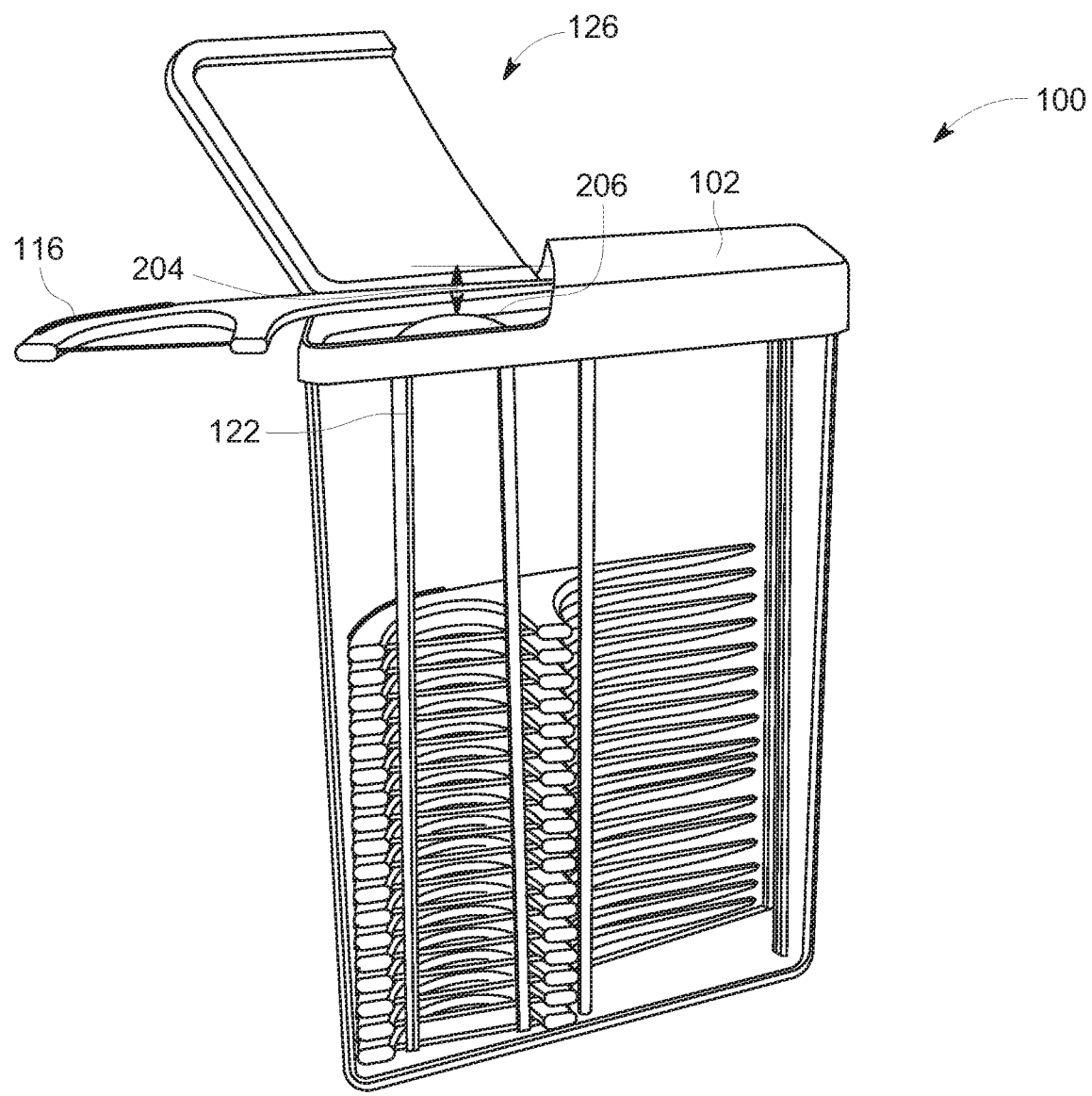
FIG. 2 is a perspective view of one embodiment of a dental tool storage container with a door.

As seen in FIG. 2, in some embodiments, the dispensing features can comprise a door 200. The door 200 can be any desired shape and size, and can be located in any desired portion of the dental tool storage container 100. In the embodiment of FIG. 2, the door 200 is located in the top 102 of the dental tool storage container 100, and the door 200 is connected to the top 102 via a hinge 202 that secures the door 200 to the top 102 of the dental tool storage container 100 and that allows the door 200 to be repeatedly moved from an open to a closed position.

In some embodiments, the dental tool storage container 100 can be sized and shaped such that a desired number of dental tools are simultaneously removable from the internal volume 114 of the dental tool storage container 100. In some embodiments, this desired number of dental tools that are simultaneously removable via the door 200, or other dispensing features, can be, for example, 1, 2, 3, 4, 5, 6, 7, 8, 9, 10, and/or any other number of dental tools. In some embodiments, the number of dental tools that are simultaneously removable from the dental tool storage container 100 can be determined by the size of a space 204 between the top 102 of the dental tool storage container 100 and a top 206 of the fixation post 122. In some embodiments, this space 204 can correspond to a thickness of the dental tool such that, for example, only a single dental tool, or any other desired number of dental tools, can pass through the space 204 at a time. In such an embodiment, the space 204 is greater than the thickness of a single dental tool or dental flosser 116, and the space 204 is less than the thickness of two dental tools or dental flossers 116.

Figure 3:
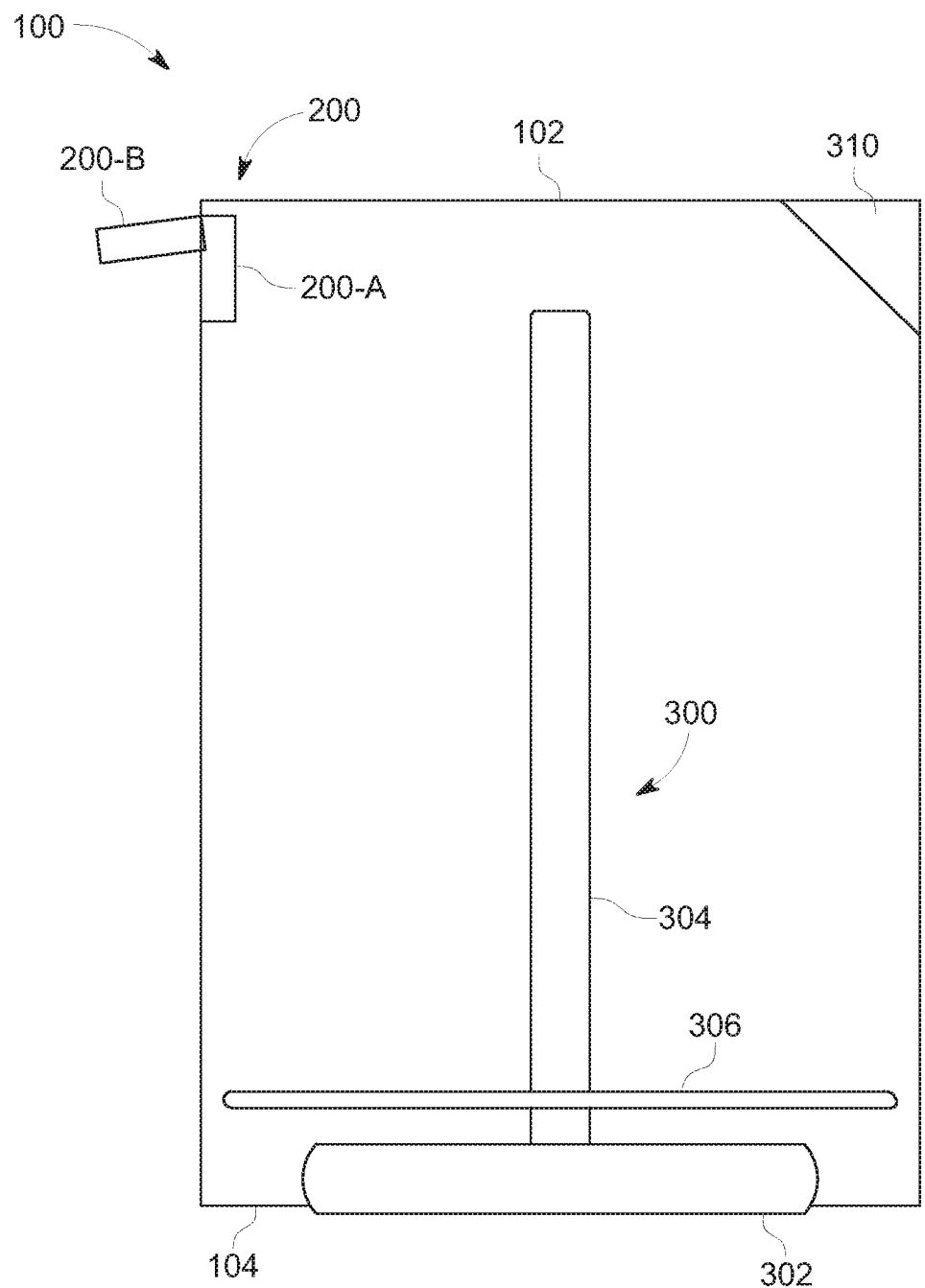
FIG. 3 is a front view of one embodiment of a dental tool storage container with a threaded positioning element.

With reference now to FIG. 3, the dispensing features can include, in some embodiments, a threaded positioning element 300, a door 200 that can be moved between a first position 200-A and a second position 200-B, and a corner kickout 310. In some embodiments, the door 200 can be biased towards, for example, the first position 200-A by, for example, a spring. In such an embodiment, the door 200 can return to the first position 200-A via the restorative force of the spring after the door has been moved to the second position 200-B.

The threaded positioning element 300 can comprise a variety of shapes and size, and can be used to adjust the difference between the location of one or several dental tools and the top 102 of the dental tool storage container 100. In some embodiments, for example, the threaded positioning element 300 can move one or several dental tools closer to, or farther away from the top 102 of the dental tool storage container 100.

The threaded positioning element 300 can comprise an interface feature 302 such as, for example, a turning wheel, and a threaded shaft 304 extending from the interface feature 302 towards the top 102 of the dental tool storage container 100. In some embodiments, the interface feature 302 can be located in the bottom 104 of the dental tool storage container 100, and can be equidistantly positioned between the first side 106 and the second side 108, and/or between the front 110 and the back of the dental tool storage container 100. In some embodiments, the interface feature 302 can be positioned relatively more proximate to one of the first side 106 and the second side 108, and/or to one of the front 110 and the back of the dental tool storage container 100.

The threaded shaft 304 can extend from the interface feature 302, and in the case that the interface feature is a turning wheel, the threaded shaft 304 can extend from the center of the turning wheel towards the top 102 of the dental tool storage container 100. In some embodiments, the threaded shaft 304 can terminate at a position with respect to the top 102 of the dental tool storage container 100 such that the desired number of dental tools can simultaneously pass between top 102 of the dental tool storage container 100 and the threaded shaft 304. In some embodiments, the threaded shaft 304 can include threads extending along all or portions of its lengths.

In some embodiments, the threads of the threaded shaft 304 can directly engage with a portion of the one or several dental tools, and in some embodiments, the threads of the threaded shaft 304 can engage with a movable platform 306. Thus, in some embodiments, the movable platform 306 can be a dental tool, and in some embodiments, the movable platform is not a dental tool.

In some embodiments, the movable platform 306 engages with the threaded shaft 304 such that rotation of the threaded shaft 304 moves the movable platform 306 either relatively closer to, or relatively farther from the top 102 of the dental tool storage container 100. In some embodiments, the movable platform 306 can be sized and shaped such that one or several dental tools can be stacked on top of the movable platform 306.

The dental tool storage container 100 can further include the corner kickout 310. In some embodiments, the corner kickout 310 can comprise one or several surfaces that engage with a portion of the dental tool when the dental tool is moved towards the corner kickout 310. As the dental tool is further advanced, the one or several surfaces of the corner kickout 310 displace the dental tool towards, for example, the door 200. In some embodiments, the one or several surfaces of the corner kickout 310 can act as cam surfaces.

Figure 4:
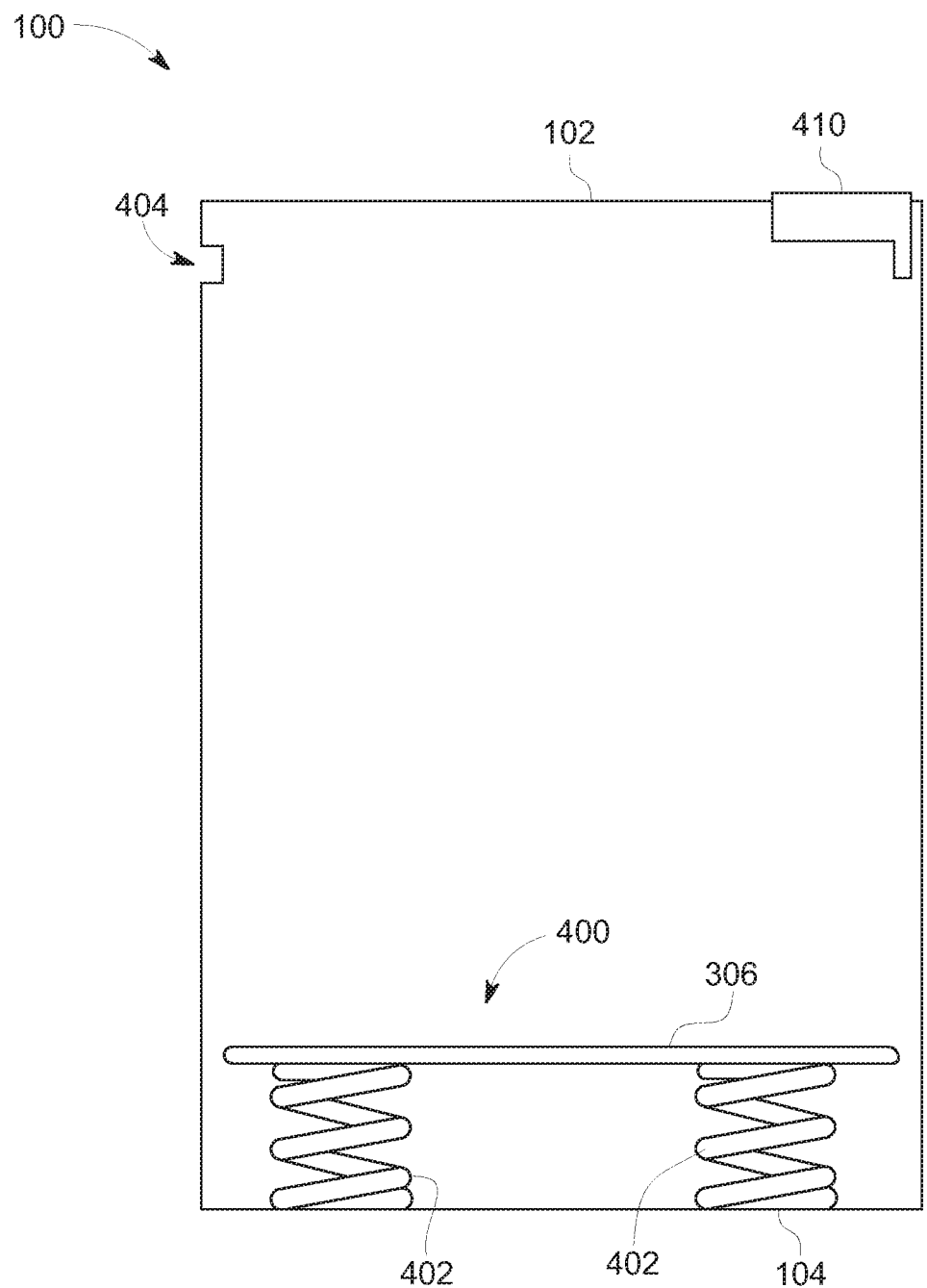
FIG. 4 is a front view of one embodiment of a dental tool storage container with a spring-loaded platform.

With reference now to FIG. 4, the dispensing features can include, in some embodiments, a spring-loaded platform 400, the manual actuator 410, and a dispensing aperture 404. In some embodiments, the spring-loaded platform 400 can moved one or several dental tools relatively closer to the top 102 of the dental tool storage container 100 when one of the dental tools is dispensed from the dental tool storage container 100. The spring-loaded platform 400 can include a movable platform 306 sized and shaped to hold one or several dental tools. The movable platform 306 can be connected to the bottom 104 of the dental tool storage container 100 via one or several springs 402. In some embodiments, these one or several springs can bias the position of the movable platform 306 towards the top 102 of the dental tool storage container 100 such that the movable platform 306 moves towards the top 102 of the dental tool storage container 100 when a dental tool is removed from the dental tool storage container 100.

The dispensing features can further include the manual actuator 410 and the dispensing aperture 404. The dispensing aperture 404 can be a hole located in a portion of the dental tool storage container 100, which hole can be sized and shaped to allow the simultaneous dispensing of a desired number of dental tools. In some embodiments, the dispensing aperture 404 can be located proximate the top 102 of the dental tool storage container 100.

The manual actuator 410 can comprise a button that can be moved from a first position to a second position and which dispenses a dental tool through, for example, the door 200, the dispensing aperture 404, or the like. In some embodiments, the manual actuator dispenses the dental tool when the button is moved from the first position to the second position. In some embodiments, the manual actuator 410 is sized to dispense the desired number of dental tools when the manual actuator 410 is moved from the first position to the second position.

In some embodiments, the manual actuator 410 can include one or several features that can automatically restore the manual actuator 410 from the second position to the first position. In some embodiments, for example, the manual actuator 410 can include one or several springs that can bias the manual actuator 410 from its second position towards its first position.

Figure 5:
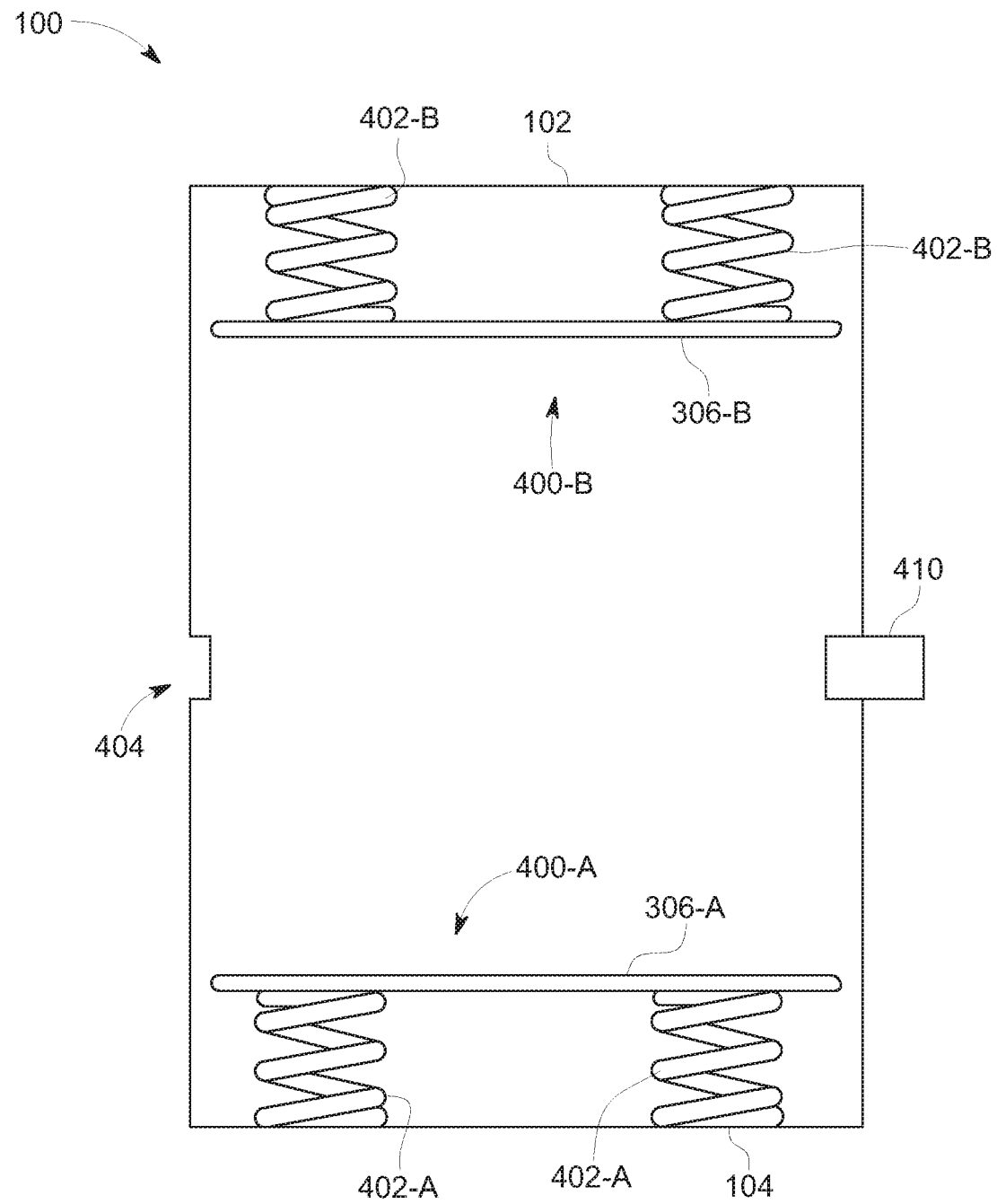
FIG. 5 is a front view of one embodiment of a dental tool storage container with two spring-loaded platforms.

With reference now to FIG. 5, the dispensing features can include, in some embodiments, a first spring-loaded platform 400-A, a second spring loaded platform 400-B, the manual actuator 410, and a dispensing aperture 404. In some embodiments, the first spring-loaded platform 400-A can moved one or several dental tools relatively closer to the top 102 of the dental tool storage container 100 when one of the dental tools is dispensed from the dental tool storage container 100, and the second spring-loaded platform 400-B can moved one or several dental tools relatively closer to the bottom 104 of the dental tool storage container 100 when one of the dental tools is dispensed from the dental tool storage container 100. The first spring-loaded platform 400-A can include a first movable platform 306-A, and the second spring-loaded platform 400-B can include a second movable platform 306-A. The movable platforms 306-A, 306-B can be sized and shaped to hold one or several dental tools. The first movable platform 306-A can be connected to the bottom 104 of the dental tool storage container 100 via one or several first springs 402-A, and the second movable platform 306-B can be connected to the top 102 of the dental tool storage container 100 via one or several second springs 402-B. In some embodiments, these one or several springs can bias the position of the first movable platform 306-A towards the top 102 of the dental tool storage container 100 such that the first movable platform 306-A moves towards the top 102 of the dental tool storage container 100 when a dental tool is removed from the dental tool storage container 100. In some embodiments, these one or several springs can bias the position of the second movable platform 306-B towards the bottom 104 of the dental tool storage container 100 such that the second movable platform 306-B moves towards the bottom 104 of the dental tool storage container 100 when a dental tool is removed from the dental tool storage container 100.

The dispensing features can further include the manual actuator 410 and the dispensing aperture 404. In the embodiment of FIG. 5, the dispensing aperture can be located at an intermediate position between the top 102 and the bottom 104 of the dental tool storage container 100. As further seen, in FIG. 5, the manual actuator 410 can be positioned such that the when depressed, the manual actuator 410 dispenses the desired number of dental tools through the dispensing aperture 404.

Figure 6:
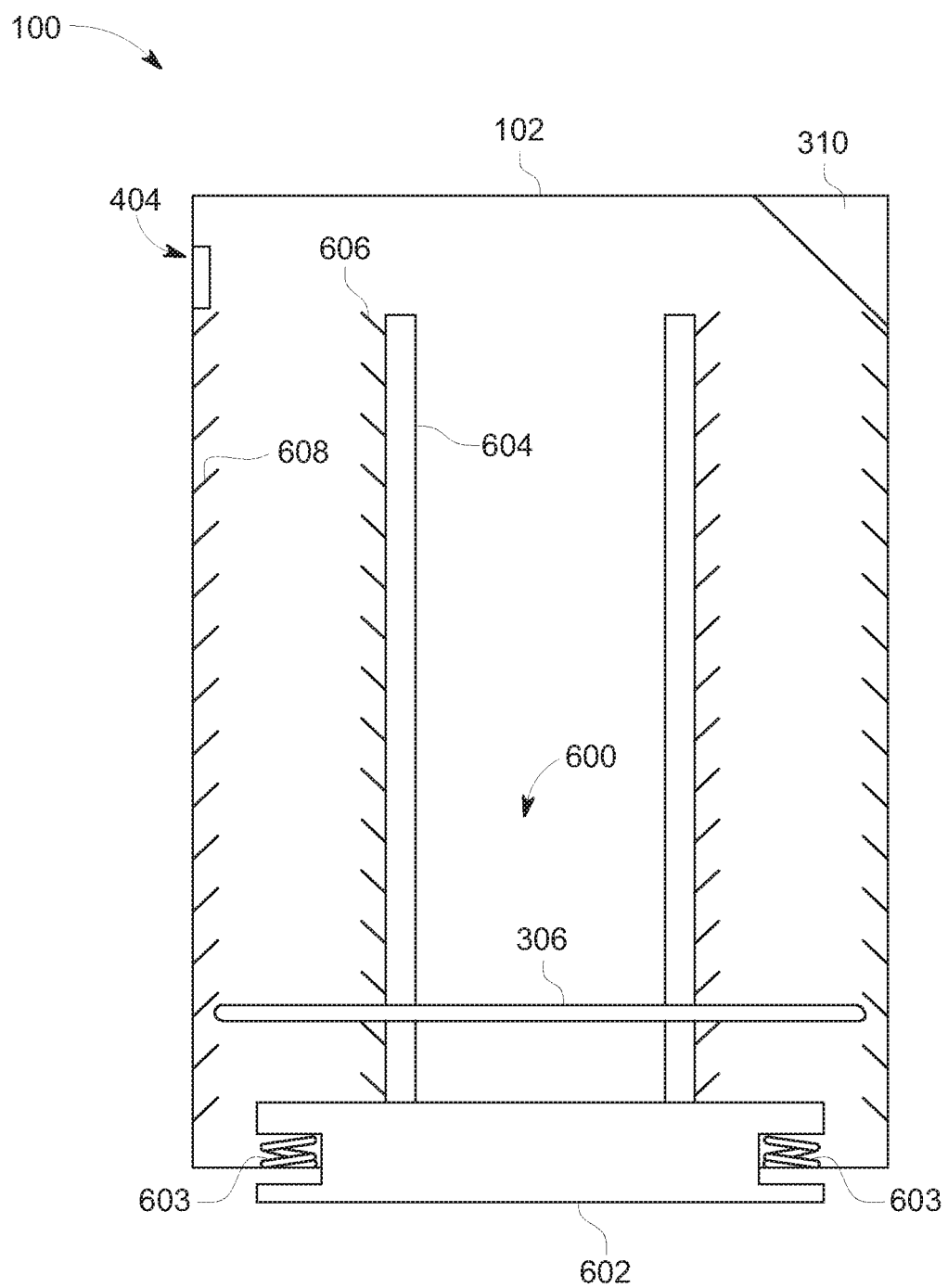
FIG. 6 is a front view of one embodiment of a dental tool storage container with a spring-ratchet mechanism.

With reference now to FIG. 6, the dispensing features can include a spring-ratchet mechanism 600. The spring-ratchet mechanism 600 can include a ratchet actuator 602. The ratchet actuator 602 can allow a user to advance dental tools towards the dispensing aperture 404 by movement of the ratchet actuator 602 from a first position to a second position. As depicted in FIG. 6, the ratchet actuator 602 can allow a user to advance dental tools towards the top of the dental tool storage container 100.

The ratchet actuator 602 can comprise a variety of shapes and sizes, and can be located at a variety of positions on the dental tool storage container 100. In some embodiments, the ratchet actuator 602 can be located at the bottom 104 of the dental tool storage container 100. In some embodiments, springs 603 can engage the bottom 104 of the dental tool storage container 100 and the ratchet actuator 602. These springs can bias the ratchet actuator from the second position to the first position.

The ratchet actuator 602 can connect to one or several ratchet posts 604 that can include ratchet members 606. The ratchet posts 604 can extend from the ratchet actuator 602 towards the top 102 of the dental tool storage container 100. In some embodiments, the ratchet posts 604 can include a plurality of ratchet members 606 spaced along the length of the ratchet posts 604. In some embodiments, these ratchet posts 604 can be configured to selectably engage with the movable platform 306 such that the movable platform 306 is movable in one direction along the length of the ratchet posts 604. Specifically, and as depicted in FIG. 6, the ratchet members 606 allow the ratchet posts 604 to move from a position relatively more proximate to the top 102 of the dental tool storage container 100 to a position relatively more proximate to the bottom 104 of the dental tool storage container 100.

The spring-ratchet mechanism 600 can further include container ratchet members 608. The container ratchet members 608 can be located along all or portions of the inner-surfaces defining the internal volume 114. In some embodiments, the container ratchet members 608 can allow the movement of the movable platform 306 in one direction with respect to the top 102 and bottom 104 of the dental tool storage container 100. In the embodiment depicted in FIG. 6, the container ratchet members 608 are configured to allow the movable platform 306 to be moved towards the top 102 of the dental tool storage container 100 and to prevent the movement of the movable platform towards the bottom 104 of the dental tool storage container 100.

In some embodiments, when the ratchet actuator 602 is moved from the first position to the second position, the movable platform can advance from engagement with one or several of the container ratchet members 608 relatively more proximate to the bottom 104 of the dental tool storage container 100 to engagement with one or several of the container ratchet members 608 relatively less proximate to the bottom 104 of the dental tool storage container 100.

When the ratchet actuator 602 is moved from the second position to the first position, the position of the movable platform 306 with respect to the top 102 and bottom 104 of the dental tool storage container 100 is maintained by the container ratchet member 608 engaging the movable platform 306.

In some embodiments, the dental tool storage container 100 can include the dispensing aperture 404 and the corner kickout 310. The dispensing aperture 404 can be sized to allow the simultaneous dispensing of a desired number of dental tools, and the corner kickout 310 can be sized and positioned to simultaneously dispense the desired number of dental tools through the dispensing aperture 404 when the dental tools are advanced towards the corner kickout 310.

Figure 7:
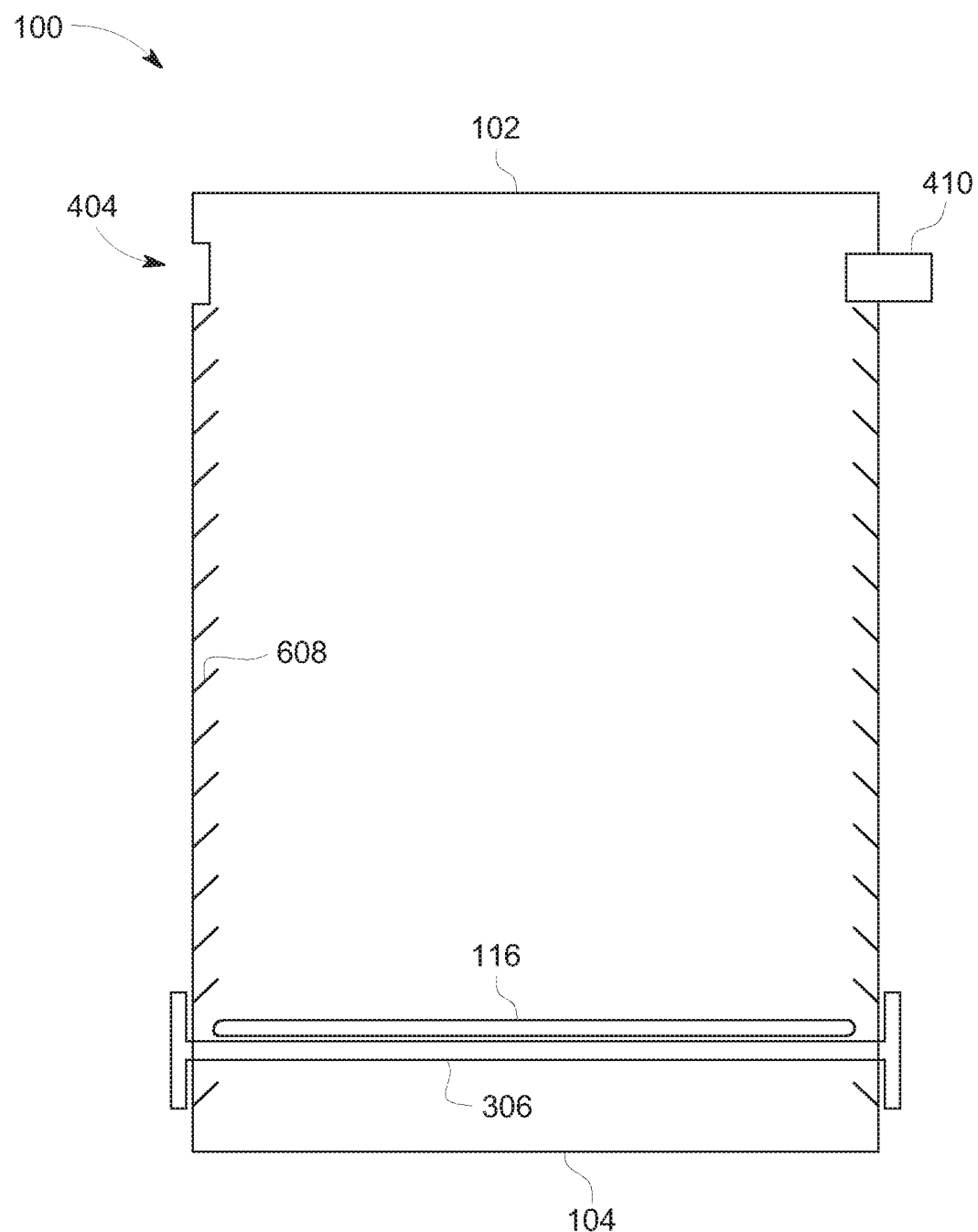
FIG. 7 is a front view of one embodiment of a dental tool storage container with a ratchet mechanism.

With reference now to FIG. 7, the dispensing features can include a ratchet mechanism 700. The ratchet mechanism can include the movable platform 306 that is movable by, for example, a user of the dental tool storage container 100. The ratchet mechanism 700 can further include container ratchet members 608 that either engage with the movable platform 306 or the dental tool, or flosser 116, to allow movement relatively towards the top 102 of the dental tool storage container 100 and to prevent movement relatively towards the bottom 104 of the dental tool storage container 100. In some embodiments, the dental tool storage container 100 can include the manual actuator 410 and the dispensing aperture 404. In some embodiments, the manual actuator 410 can dispense a desired number of dental tools through the dispensing aperture 404 when the desired number of dental tools are positioned for dispensing by, for example, the relative movement of the movable platform 306 towards the top 102 of the dental tool storage container 100.

Figure 8:
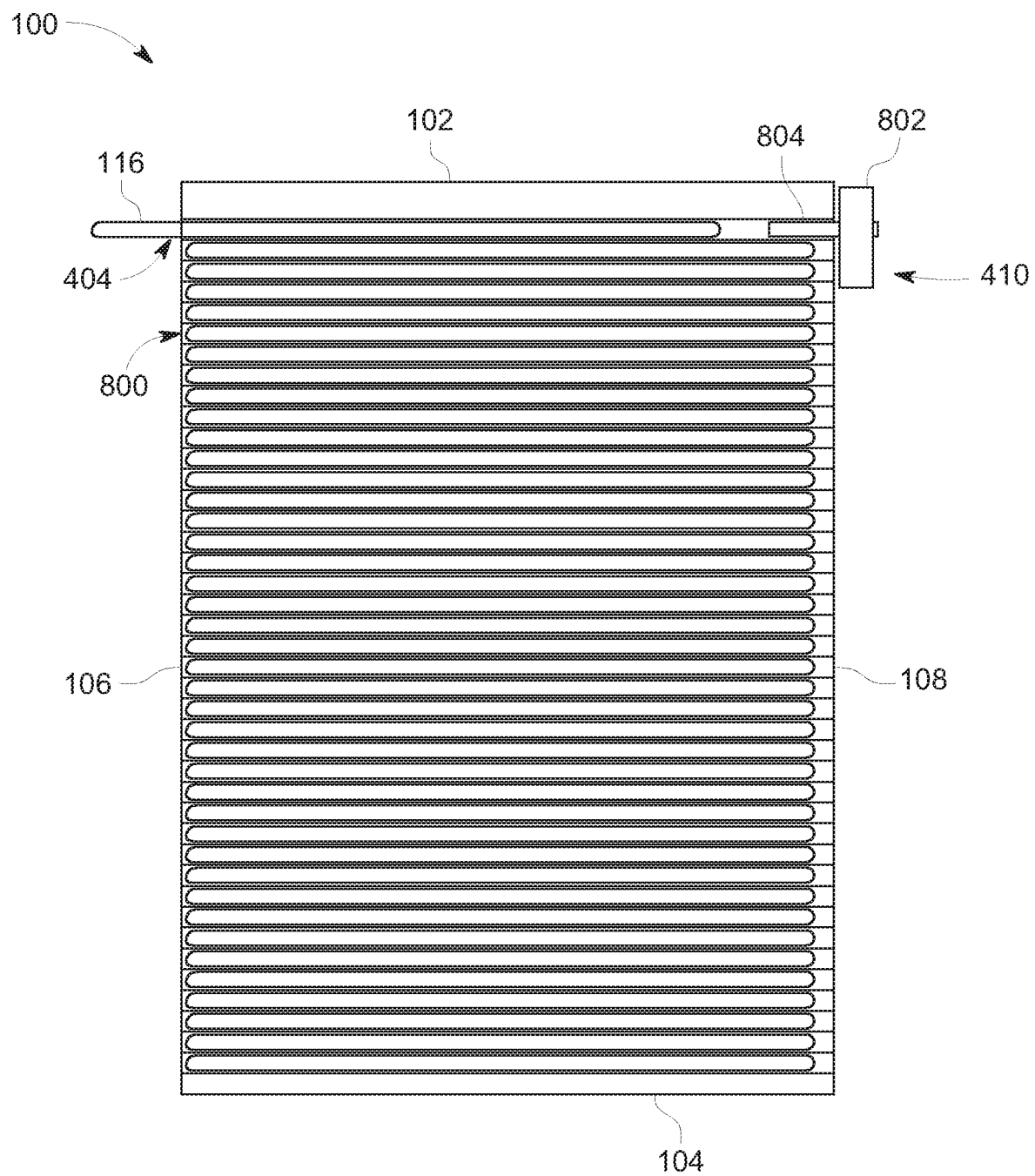
FIG. 8 is a front view of one embodiment of a dental tool storage container with a plurality of cells.

With reference now to FIG. 8, the dental tool storage container 100 can be divided into a plurality of cells 800. In some embodiments, each of the cells can comprise a dispenser aperture 404 which can be an open aperture or a temporarily closed aperture such as by, for example a tearable film covering. In some embodiments, each of the cells 800 can contain at least one dental tool.

The dispensing features in the embodiment of FIG. 8 can include a manual actuator 410 that can engage dental tools within the cells 800 to dispense the dental tools. In some embodiments, this manual actuator 410 can include a sliding base 802 that is movable, in some embodiments, along the length of the dental tool storage container 100 between the top 102 and the bottom 104 of the dental tool storage container 100.

The manual actuator 410 can further include a dispenser 804. The dispenser 804 can be moved from a first position in which it does not engage a dental tool to a second position in which the dispenser 804 engages and dispenses a dental tool. The dispenser 804 can be connected to the sliding base 802 so as to be movable with the sliding base 802 to position the dispenser 804 with respect to a cell 800 to allow dispensing of a dental tool. In the embodiment shown in FIG. 8, the dispenser 804 is in the second position. As seen, the dispenser 804 extends into a cell 800 and has dispensed the flosser 116 in that cell 800.

While various embodiments of present invention have been described, it will be apparent to those of skill in the art that many more embodiments and implementations are possible that are within the scope of this invention. Accordingly, the present invention is not to be limited to the described embodiments.

What is claimed is:

1. A dental tool storage system comprising:
   a plurality of flossers comprising:
   a flossing head comprising:
      a first arm;
      a second arm;
      a connecting member; and
      a filament extending from the first arm to the second arm; and
   a handle portion extending from the flossing head; and
   a dental tool storage container comprising:
      an internal volume defined by:
         a top;
         a bottom; and
         a plurality of sides, wherein the internal volume is sized and shaped to receive the plurality of flossers in a stack extending at least partially between the top and the bottom of the internal volume;
      one or more dispensing features located in one of: the top; the bottom; or one or more of the plurality of sides, wherein the dispensing features are sized and shaped to simultaneously dispense a desired number of flossers; and
      a plurality of fixation features extending at least partially from one of: the top; or the bottom, towards the other of the top or the bottom, wherein the fixation features are sized and shaped to engage with at least some of the plurality of flossers to fix a position of the at least some of the plurality of flossers with respect to the plurality of sides,
   wherein the fixation features comprise a plurality of fixation posts, wherein the plurality of fixation posts are positioned to engage an exterior of a handle of the flossers and the fixation features are configured to hold a first flosser in a first orientation and a second flosser in a second orientation, wherein the flossing head of the first flosser is adjacent to and proximate to the handle of the second flosser when the first flosser is in the first orientation and when the second flosser is in the second orientation such that the plurality of flossers can be alternatingly stacked in two adjacent stacks in the dental tool storage container.

2. The dental tool storage system of claim 1, wherein the fixation features comprises a plurality of fixation posts.

3. The dental tool storage system of claim 2, wherein the fixation posts are sized to fit between the first arm, the second arm, and the filament of the flossing head.

4. The dental tool storage system of claim 3, wherein the fixation posts connect to the bottom of the dental tool storage system and is separated from the top of the dental tool storage container by a space.

5. The dental tool storage system of claim 4, wherein the space is greater than a first thickness of one flosser and less than a second thickness of two flossers.

6. A dental tool storage container comprising:
   an internal volume defined by:
      a top;
      a bottom; and
      a plurality of sides, wherein the internal volume is sized and shaped to receive a plurality of dental tools in a stack extending at least partially between the top and the bottom of the internal volume;
   one or more dispensing features located in one of: the top; the bottom; or one or more of the plurality of sides, wherein the dispensing feature are sized and shaped to simultaneously dispense a desired number of dental tools; and a plurality of fixation features extending at least partially from one of: the top; or the bottom towards the other of the top or the bottom, wherein the fixation features are sized and shaped to engage with at least some of the plurality of dental tools to fix a position of the at least some of the plurality of dental tools with respect to the plurality of sides wherein the fixation features comprise a plurality of fixation posts, wherein the plurality of fixation posts are positioned to engage an exterior of a handle of the dental tools and the fixation features are configured to hold a first dental tool in a first orientation and a second dental tool in a second orientation, wherein a flossing head of the first dental tool is adjacent to and proximate to the handle of the second dental tool when the first dental tool is in the first orientation and when the second dental tool is in the second orientation such that the plurality of dental tools can be alternatingly stacked in two adjacent stacks in the dental tool storage container.

7. The dental tool storage container of claim 6, wherein the fixation features comprises a plurality of fixation posts.

8. The dental tool storage container of claim 7, wherein the fixation posts are sized to fit in an interior portion of the plurality of dental tools.

9. The dental tool storage container of claim 8, wherein the fixation posts connects to the bottom of the dental tool storage container and is separated from the top of the dental tool storage container by a space.

10. The dental tool storage container of claim 9, wherein the space is greater than a first thickness of one dental tool and less than a second thickness of two dental tools.

11. The dental tool storage container of claim 6, wherein the dispensing features comprise: first dispensing features for dispensing first dental tools; and second dispensing features for dispensing second tools.

* * * * *